United States Patent
Kato et al.

(10) Patent No.: US 8,349,569 B2
(45) Date of Patent: Jan. 8, 2013

(54) ANTI-FIBRONECTIN FRAGMENT MONOCLONAL ANTIBODY

(75) Inventors: Chika Kato, Shiga (JP); Yuka Sano, Shiga (JP); Kyoko Kamihagi, Shiga (JP); Ikunoshin Kato, Shiga (JP)

(73) Assignee: Takara Bio Inc., Otsu-shi, Shiga (JP)

( * ) Notice: Subject to any disclaimer, the term of this patent is extended or adjusted under 35 U.S.C. 154(b) by 247 days.

(21) Appl. No.: 12/750,882

(22) Filed: Mar. 31, 2010

(65) Prior Publication Data

US 2010/0248262 A1 Sep. 30, 2010

(30) Foreign Application Priority Data

Mar. 31, 2009 (JP) ............................. P2009-083909

(51) Int. Cl.
*G01N 33/53* (2006.01)
*G01N 33/48* (2006.01)
*C12N 5/12* (2006.01)
*C07K 16/18* (2006.01)
*A61K 39/395* (2006.01)

(52) U.S. Cl. ...... 435/7.1; 435/70.21; 435/331; 435/332; 530/387.9; 530/388.2; 424/139.1; 436/87

(58) Field of Classification Search .......................... None
See application file for complete search history.

(56) References Cited

U.S. PATENT DOCUMENTS

2008/0318337 A1* 12/2008 Heinegard et al. ............ 436/501

FOREIGN PATENT DOCUMENTS

| DE | 3743402 | | 7/1988 |
| EP | 1916302 | | 4/2008 |
| JP | 06-044877 | | 6/1994 |
| WO | WO 94/17411 | * | 8/1994 |
| WO | 03-016511 | | 2/2003 |

OTHER PUBLICATIONS

European Search Report corresponding to European Application No. 10003458.6-2406 dated Jul. 23, 2010.
Fusao Kimizuka et al., J. Biochem., vol. 110, No. 2, p. 284-291, "Production and Characterization of Functional Domains of Human Fibronectin Expressed in *Escherichia coli*" (Mar. 11, 1991).
Helmut Hanenberg et al., Human Gene Therapy, vol. 8, No. 18, p. 2193-2206 "Optimization of Fibronectin-Assisted Retroviral Gene Transfer into Human CD34+ Hematopoietic Cells" (Dec. 10, 1997).
Helmut Hanenberg et al., Nature Medicine, vol. 2, p. 876-882 "Colocalization of Retrovirus and Target Cells on Specific Fibronectin Fragments Increases Genetic Transduction of Mammalian Cells". (Aug. 8, 1996).
Masahiko Katayama et al., Experimental Cell Research 185, p. 229-236 "Isolation and Characterization of Two Monoclonal Antibodies that Recognize Remote Epitopes on the Cell-Binding Domain of Human Fibronectin". (1989).

* cited by examiner

*Primary Examiner* — Christine Foster
(74) *Attorney, Agent, or Firm* — Banner & Witcoff, Ltd

(57) ABSTRACT

A method for measuring a fibronectin fragment which is easy to handle and has excellent measuring accuracy, specificity and reproducibility is provided. An anti-fibronectin fragment monoclonal antibody which reacts with a human fibronectin fragment but does not react with human fibronectin, a measuring reagent containing the monoclonal antibody, a method for measuring a fibronectin fragment which uses the monoclonal antibody and a hybridoma which produces the monoclonal antibody are provided.

12 Claims, No Drawings

SEQUENCE LISTING

```
<160> NUMBER OF SEQ ID NOS: 6

<210> SEQ ID NO 1
<211> LENGTH: 574
<212> TYPE: PRT
<213> ORGANISM: Artificial Sequence
<220> FEATURE:
<223> OTHER INFORMATION: fibronectin fragment named CH-296

<400> SEQUENCE: 1

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
    210                 215                 220
```

```
Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
            245                 250                 255

Asp Ser Pro Ala Ser Ser Lys Pro Ile Ser Ile Asn Tyr Arg Thr Glu
            260                 265                 270

Ile Asp Lys Pro Ser Met Ala Ile Pro Ala Pro Thr Asp Leu Lys Phe
        275                 280                 285

Thr Gln Val Thr Pro Thr Ser Leu Ser Ala Gln Trp Thr Pro Pro Asn
    290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
                325                 330                 335

Val Ser Gly Leu Met Val Ala Thr Lys Tyr Glu Val Ser Val Tyr Ala
            340                 345                 350

Leu Lys Asp Thr Leu Thr Ser Arg Pro Ala Gln Gly Val Val Thr Thr
        355                 360                 365

Leu Glu Asn Val Ser Pro Pro Arg Arg Ala Arg Val Thr Asp Ala Thr
    370                 375                 380

Glu Thr Thr Ile Thr Ile Ser Trp Arg Thr Lys Thr Glu Thr Ile Thr
385                 390                 395                 400

Gly Phe Gln Val Asp Ala Val Pro Ala Asn Gly Gln Thr Pro Ile Gln
                405                 410                 415

Arg Thr Ile Lys Pro Asp Val Arg Ser Tyr Thr Ile Thr Gly Leu Gln
            420                 425                 430

Pro Gly Thr Asp Tyr Lys Ile Tyr Leu Tyr Thr Leu Asn Asp Asn Ala
        435                 440                 445

Arg Ser Ser Pro Val Val Ile Asp Ala Ser Thr Ala Ile Asp Ala Pro
    450                 455                 460

Ser Asn Leu Arg Phe Leu Ala Thr Thr Pro Asn Ser Leu Leu Val Ser
465                 470                 475                 480

Trp Gln Pro Pro Arg Ala Arg Ile Thr Gly Tyr Ile Ile Lys Tyr Glu
                485                 490                 495

Lys Pro Gly Ser Pro Pro Arg Glu Val Val Pro Arg Pro Arg Pro Gly
            500                 505                 510

Val Thr Glu Ala Thr Ile Thr Gly Leu Glu Pro Gly Thr Glu Tyr Thr
        515                 520                 525

Ile Tyr Val Ile Ala Leu Lys Asn Asn Gln Lys Ser Glu Pro Leu Ile
    530                 535                 540

Gly Arg Lys Lys Thr Asp Glu Leu Pro Gln Leu Val Thr Leu Pro His
545                 550                 555                 560

Pro Asn Leu His Gly Pro Glu Ile Leu Asp Val Pro Ser Thr
                565                 570

<210> SEQ ID NO 2
<211> LENGTH: 274
<212> TYPE: PRT
<213> ORGANISM: Artificial Sequence
<220> FEATURE:
<223> OTHER INFORMATION: fibronectin fragment named C-274

<400> SEQUENCE: 2

Pro Thr Asp Leu Arg Phe Thr Asn Ile Gly Pro Asp Thr Met Arg Val
1               5                   10                  15
```

```
Thr Trp Ala Pro Pro Ser Ile Asp Leu Thr Asn Phe Leu Val Arg
         20              25              30

Tyr Ser Pro Val Lys Asn Glu Glu Asp Val Ala Glu Leu Ser Ile Ser
         35              40              45

Pro Ser Asp Asn Ala Val Val Leu Thr Asn Leu Leu Pro Gly Thr Glu
 50              55              60

Tyr Val Val Ser Val Ser Ser Val Tyr Glu Gln His Glu Ser Thr Pro
 65              70              75              80

Leu Arg Gly Arg Gln Lys Thr Gly Leu Asp Ser Pro Thr Gly Ile Asp
                 85              90              95

Phe Ser Asp Ile Thr Ala Asn Ser Phe Thr Val His Trp Ile Ala Pro
                 100             105             110

Arg Ala Thr Ile Thr Gly Tyr Arg Ile Arg His His Pro Glu His Phe
         115             120             125

Ser Gly Arg Pro Arg Glu Asp Arg Val Pro His Ser Arg Asn Ser Ile
         130             135             140

Thr Leu Thr Asn Leu Thr Pro Gly Thr Glu Tyr Val Val Ser Ile Val
145             150             155             160

Ala Leu Asn Gly Arg Glu Glu Ser Pro Leu Leu Ile Gly Gln Gln Ser
                 165             170             175

Thr Val Ser Asp Val Pro Arg Asp Leu Glu Val Val Ala Ala Thr Pro
         180             185             190

Thr Ser Leu Leu Ile Ser Trp Asp Ala Pro Ala Val Thr Val Arg Tyr
         195             200             205

Tyr Arg Ile Thr Tyr Gly Glu Thr Gly Gly Asn Ser Pro Val Gln Glu
 210             215             220

Phe Thr Val Pro Gly Ser Lys Ser Thr Ala Thr Ile Ser Gly Leu Lys
225             230             235             240

Pro Gly Val Asp Tyr Thr Ile Thr Val Tyr Ala Val Thr Gly Arg Gly
                 245             250             255

Asp Ser Pro Ala Ser Ser Lys Pro Ile Ser Ile Asn Tyr Arg Thr Glu
                 260             265             270

Ile Asp

<210> SEQ ID NO 3
<211> LENGTH: 296
<212> TYPE: PRT
<213> ORGANISM: Artificial Sequence
<220> FEATURE:
<223> OTHER INFORMATION: fibronectin fragment named H-296

<400> SEQUENCE: 3

Ala Ile Pro Ala Pro Thr Asp Leu Lys Phe Thr Gln Val Thr Pro Thr
1               5               10              15

Ser Leu Ser Ala Gln Trp Thr Pro Pro Asn Val Gln Leu Thr Gly Tyr
         20              25              30

Arg Val Arg Val Thr Pro Lys Glu Lys Thr Gly Pro Met Lys Glu Ile
         35              40              45

Asn Leu Ala Pro Asp Ser Ser Val Val Val Ser Gly Leu Met Val
 50              55              60

Ala Thr Lys Tyr Glu Val Ser Val Tyr Ala Leu Lys Asp Thr Leu Thr
 65              70              75              80

Ser Arg Pro Ala Gln Gly Val Val Thr Thr Leu Glu Asn Val Ser Pro
                 85              90              95

Pro Arg Arg Ala Arg Val Thr Asp Ala Thr Glu Thr Thr Ile Thr Ile
                 100             105             110
```

Ser Trp Arg Thr Lys Thr Glu Thr Ile Thr Gly Phe Gln Val Asp Ala
        115                 120                 125

Val Pro Ala Asn Gly Gln Thr Pro Ile Gln Arg Thr Ile Lys Pro Asp
    130                 135                 140

Val Arg Ser Tyr Thr Ile Thr Gly Leu Gln Pro Gly Thr Asp Tyr Lys
145                 150                 155                 160

Ile Tyr Leu Tyr Thr Leu Asn Asp Asn Ala Arg Ser Ser Pro Val Val
                165                 170                 175

Ile Asp Ala Ser Thr Ala Ile Asp Ala Pro Ser Asn Leu Arg Phe Leu
            180                 185                 190

Ala Thr Thr Pro Asn Ser Leu Leu Val Ser Trp Gln Pro Pro Arg Ala
        195                 200                 205

Arg Ile Thr Gly Tyr Ile Ile Lys Tyr Glu Lys Pro Gly Ser Pro Pro
    210                 215                 220

Arg Glu Val Val Pro Arg Pro Arg Pro Gly Val Thr Glu Ala Thr Ile
225                 230                 235                 240

Thr Gly Leu Glu Pro Gly Thr Glu Tyr Thr Ile Tyr Val Ile Ala Leu
                245                 250                 255

Lys Asn Asn Gln Lys Ser Glu Pro Leu Ile Gly Arg Lys Lys Thr Asp
            260                 265                 270

Glu Leu Pro Gln Leu Val Thr Leu Pro His Pro Asn Leu His Gly Pro
        275                 280                 285

Glu Ile Leu Asp Val Pro Ser Thr
    290                 295

<210> SEQ ID NO 4
<211> LENGTH: 367
<212> TYPE: PRT
<213> ORGANISM: Artificial Sequence
<220> FEATURE:
<223> OTHER INFORMATION: fibronectin fragment named CHV-89

<400> SEQUENCE: 4

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
                35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

```
Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
            195                 200                 205

Tyr Arg Ile Thr Tyr Gly Glu Thr Gly Gly Asn Ser Pro Val Gln Glu
            210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Asn Val Ser Pro Pro Arg Arg Ala Arg Val
            275                 280                 285

Thr Asp Ala Thr Glu Thr Thr Ile Thr Ile Ser Trp Arg Thr Lys Thr
            290                 295                 300

Glu Thr Ile Thr Gly Phe Gln Val Asp Ala Val Pro Ala Asn Gly Gln
305                 310                 315                 320

Thr Pro Ile Gln Arg Thr Ile Lys Pro Asp Val Arg Ser Tyr Thr Ile
                325                 330                 335

Thr Gly Leu Gln Pro Gly Thr Asp Tyr Lys Ile Tyr Leu Tyr Thr Leu
            340                 345                 350

Asn Asp Asn Ala Arg Ser Ser Pro Val Val Ile Asp Ala Ser Thr
            355                 360                 365

<210> SEQ ID NO 5
<211> LENGTH: 370
<212> TYPE: PRT
<213> ORGANISM: Artificial Sequence
<220> FEATURE:
<223> OTHER INFORMATION: fibronectin fragment named CHV-92

<400> SEQUENCE: 5

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
                20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
        50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
```

```
                    180                 185                 190
Thr Ser Leu Leu Ile Ser Trp Asp Ala Pro Ala Val Thr Val Arg Tyr
            195                 200                 205

Tyr Arg Ile Thr Tyr Gly Glu Thr Gly Gly Asn Ser Pro Val Gln Glu
            210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
            245                 250                 255

Asp Ser Pro Ala Ser Ser Lys Pro Ile Ser Ile Asn Tyr Arg Thr Glu
            260                 265                 270

Ile Asp Lys Pro Ser Met Ala Ile Pro Ala Pro Thr Asp Leu Lys Phe
            275                 280                 285

Thr Gln Val Thr Pro Thr Ser Leu Ser Ala Gln Trp Thr Pro Pro Asn
            290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
            325                 330                 335

Val Ser Gly Leu Met Val Ala Thr Lys Tyr Glu Val Ser Val Tyr Ala
            340                 345                 350

Leu Lys Asp Thr Leu Thr Ser Arg Pro Ala Gln Gly Val Val Thr Thr
            355                 360                 365

Leu Glu
    370

<210> SEQ ID NO 6
<211> LENGTH: 459
<212> TYPE: PRT
<213> ORGANISM: Artificial Sequence
<220> FEATURE:
<223> OTHER INFORMATION: fibronectin fragment named CHV-181

<400> SEQUENCE: 6

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
            50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
            85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
            115                 120                 125

Ser Gly Arg Pro Arg Glu Asp Arg Val Pro His Ser Arg Asn Ser Ile
            130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
            165                 170                 175
```

```
Thr Val Ser Asp Val Pro Arg Asp Leu Glu Val Val Ala Ala Thr Pro
            180                 185                 190
Thr Ser Leu Leu Ile Ser Trp Asp Ala Pro Ala Val Thr Val Arg Tyr
        195                 200                 205
Tyr Arg Ile Thr Tyr Gly Glu Thr Gly Gly Asn Ser Pro Val Gln Glu
    210                 215                 220
Phe Thr Val Pro Gly Ser Lys Ser Thr Ala Thr Ile Ser Gly Leu Lys
225                 230                 235                 240
Pro Gly Val Asp Tyr Thr Ile Thr Val Tyr Ala Val Thr Gly Arg Gly
                245                 250                 255
Asp Ser Pro Ala Ser Ser Lys Pro Ile Ser Ile Asn Tyr Arg Thr Glu
            260                 265                 270
Ile Asp Lys Pro Ser Met Ala Ile Pro Ala Pro Thr Asp Leu Lys Phe
            275                 280                 285
Thr Gln Val Thr Pro Thr Ser Leu Ser Ala Gln Trp Thr Pro Pro Asn
    290                 295                 300
Val Gln Leu Thr Gly Tyr Arg Val Arg Val Thr Pro Lys Glu Lys Thr
305                 310                 315                 320
Gly Pro Met Lys Glu Ile Asn Leu Ala Pro Asp Ser Ser Ser Val Val
            325                 330                 335
Val Ser Gly Leu Met Val Ala Thr Lys Tyr Glu Val Ser Val Tyr Ala
            340                 345                 350
Leu Lys Asp Thr Leu Thr Ser Arg Pro Ala Gln Gly Val Val Thr Thr
            355                 360                 365
Leu Glu Asn Val Ser Pro Pro Arg Arg Ala Arg Val Thr Asp Ala Thr
    370                 375                 380
Glu Thr Thr Ile Thr Ile Ser Trp Arg Thr Lys Thr Glu Thr Ile Thr
385                 390                 395                 400
Gly Phe Gln Val Asp Ala Val Pro Ala Asn Gly Gln Thr Pro Ile Gln
                405                 410                 415
Arg Thr Ile Lys Pro Asp Val Arg Ser Tyr Thr Ile Thr Gly Leu Gln
            420                 425                 430
Pro Gly Thr Asp Tyr Lys Ile Tyr Leu Tyr Thr Leu Asn Asp Asn Ala
        435                 440                 445
Arg Ser Ser Pro Val Val Ile Asp Ala Ser Thr
450                 455
```

US 8,349,569 B2

ANTI-FIBRONECTIN FRAGMENT MONOCLONAL ANTIBODY

FOREIGN PRIORITY

This application is based on Japanese Patent Application No P2009-083909, filed on Mar. 31, 2009, the entire contents thereof being hereby incorporated by reference.

FIELD OF THE INVENTION

The present invention relates to an anti-fibronectin fragment monoclonal antibody having specificity for a human fibronectin fragment and an application method thereof.

BACKGROUND

Fibronectin (to be referred to as FN hereinafter) is a huge glycoprotein having a molecular weight of about 250,000, which exists in an animal blood, on the surface of a cultured cell or in an extracellular matrix of a tissue, and is known to have various functions. Its domain structure is divided into seven, and three types of similar sequences are contained in its amino acid sequence and the entire sequence is constituted by repetitions of these respective sequences. The three types of the similar sequences are called type I, type II and type III. Among them, the type III is constituted from 71 to 96 amino acid residues and the ratio of identity of these amino acid residues is from 17 to 40%. Fourteen of type III sequences are contained in FN, and among these, the 8th, 9th and 10th sequences (to be referred to as III-8, III-9 and III-10, respectively, hereinafter) are contained in a cell-binding domain, and the 12th, 13th and 14th sequences (to be referred to as III-12, III-13 and III-14, respectively, hereinafter) are contained in a heparin-binding domain. Also, a VLA (very late activation antigen)-5 binding region is contained in the III-10, and the core sequence thereof is RGDS. In addition, a region called IIICS exists at the C terminal side of the heparin-binding domain. A region called CS-1 having a binding activity for VLA-4, which consists of 25 amino acids, exists in the IIICS.

As described above, FN has various physiological activities such as adhesion to cells, signal transduction and the like. Similar to the case of general physiologically active substances, it is advantageous to use a specific antibody in studying these physiological activities. A monoclonal antibody which reacts with FN has already been reported in Patent Document 1 (JP-B-6-44877).

On the other hand, an FN fragment consisting of a functional domain of FN or a part thereof has been prepared in Non-patent Document 1 (J. Biochem., 1991, Vol. 110, No. 2, pp. 284-291). It is known that a certain FN fragment improves the efficiency of gene transfection using a retrovirus vector into a hematopoietic stem cell, see Non-patent Document 2 (Human Gene Therapy, 1997, Vol. 8, No. 18, pp. 2193-2206) and Non-patent Document 3 (Nature Medicine, 1996, Vol. 2, pp. 876-882). In addition, a culturing method in which an FN fragment is added to a medium for immune cells is reported in Patent Document 2 (WO03/016511). Thus, FN fragments are used for addition to a cell culture medium, immobilization onto a cell culture container and the like.

[Patent Document 1] JP-B-6-44877
[Patent Document 2] International Publication No. WO03/016511
[Non-patent Document 1] J. Biochem., 1991, Vol. 110, No. 2, pp. 284-291

[Non-patent Document 2] Human Gene Therapy, 1997, Vol. 8, No. 18, pp. 2193-2206
[Non-patent Document 3] Nature Medicine, 1996, Vol. 2, pp. 876-882

BRIEF SUMMARY

Since the FN fragment is a polypeptide of a part of FN, an antibody which reacts with an FN fragment also cross-reacts with FN. In addition, since FN is contained in a large amount in blood components such as serum and the like, it was impossible to specifically measure an FN fragment contained in the serum or a serum-containing sample, with discriminating from FN.

However, a mean for measuring an FN fragment, which is convenient to handle and excellent in measuring accuracy, specificity and reproducibility, has been desired.

By conducting intensive studies, the present inventors have succeeded in creating an anti-FN fragment monoclonal antibody which specifically recognizes an FN fragment but does not recognize FN, which had not been obtained so far. The present inventors found that conventional problems can be solved by using said monoclonal antibody, namely, said monoclonal antibody is useful in monitoring an FN fragment in cultured cell media, in washing liquids of cell culture containers and further in blood samples, thereby accomplished the present invention.

Thus, embodiments of the present invention relate to:

[1] an anti-fibronectin (FN) fragment monoclonal antibody, which reacts with a human FN fragment but does not react with human FN,

[2] the anti-FN fragment monoclonal antibody according to [1], which reacts with a human FN fragment comprising the amino acid sequence described in SEQ ID NO:2 of SEQUENCE LISTING,

[3] the anti-EN fragment monoclonal antibody according to [1], which is a monoclonal antibody RNIIC57Z 71-3A produced by a hybridoma cell RNIIC57Z 71-3A (FERM BP-11202),

[4] a reagent for measuring an FN fragment in a sample, which comprises the anti-FN fragment monoclonal antibody according to [1],

[5] the reagent for measuring an FN fragment according to [4], which further comprises an antibody which reacts with a human FN fragment,

[6] a method for measuring an FN fragment in a sample, which comprises allowing the sample to contact with the anti-FN fragment monoclonal antibody according to [1] or the reagent for measuring an FN fragment according to [4],

[7] the method for measuring an FN fragment according to [6], wherein the FN fragment is a human FN fragment and the sample contains human FN,

[8] the method for measuring an FN fragment according to [6] or [7], wherein the sample is selected from a group consisting of a sample derived from the living body and a sample derived from a cultured cell, and

[9] a hybridoma cell having a deposition number FERM BP-11202 which is capable of producing the anti-FN fragment monoclonal antibody according to [1].

According to an exemplary embodiment of the present invention, an anti-FN fragment monoclonal antibody which is convenient to handle, has high measuring accuracy and is excellent in specificity and reproducibility is stably provided.

The reagent of an exemplary embodiment of the present invention can examine the amount of an FN fragment in a sample. In addition, since the antibody of an exemplary embodiment of the present invention does not recognize full length FN, it has a considerable effect in that an FN fragment can be measured specifically and accurately even in a sample having a possibility of being contaminated with FN, such as serum.

DETAILED DESCRIPTION OF EXEMPLARY EMBODIMENTS

The "fibronectin" (FN) used in the present application is a huge glycoprotein constituted from more than 2,000 amino acid residues, which exists in blood, on the surface of a cultured cell or in an extracellular matrix of a tissue. Various splicing variants are known for FN. For example, in the case of a plasma-derived FN, it is known that a region called ED-B existing in the upstream of the cell-binding domain and a region called ED-A existing between the cell-binding domain and the heparin-binding domain are deleted. Such a plasma-derived FN is also included in FN used in this application as long as it is full length FN existing in the nature. The nucleotide sequence coding for FN and the amino acid sequence of FN are disclosed in GenBank Accession No. NM-002026 and NP-002017, the entire contents thereof being hereby incorporated by reference.

According to the present invention, the "fibronectin fragment" (FN fragment) means a polypeptide which contains a part of FN. While FN has the full length of fibronectin, an FN fragment is a polypeptide having a partial sequence of FN, and for example, it may be a recombinant polypeptide having a specific domain region or a part thereof, namely a recombinant FN fragment. In addition, a recombinant polypeptide in which plurality of the same or different FN fragments are combined is also included in the FN fragment of the present invention.

In the present application, the "monoclonal antibody" means an antibody which is secreted from a single clone antibody-producing cell. This is an antibody which recognizes a specific antigenic determinant (epitope), and its primary structure of the amino acid sequence is uniform. In addition to an antibody produced by a hybridoma prepared by a cell fusion method, an antibody prepared by a genetic engineering means using an mRNA of an antibody producing cell or the like, is also included in the monoclonal antibody of the present invention.

In the present application, the term "reacts with an FN fragment but does not react with human FN" means that the monoclonal antibody of the present invention does not show strong immune reaction with human FN. Though it is not particularly limited, for example, when human FN is measured using the monoclonal antibody of the present invention, the measured value is an extremely low value in comparison with the measured value of an FN fragment having the same concentration or the same number of molecules with the FN, or a value having substantially no meaning as the measured value, which is 1% or less, preferably 0.1% or less, particularly preferably 0.01% or less. In the most preferable embodiment, the measured value of FN is a detection limit or less.

(1) Anti-FN Fragment Monoclonal Antibody of the Present Invention

That is, an exemplary embodiment of the present invention relates to a monoclonal antibody which reacts with an FN fragment but does not react with FN. Since the antibody of an exemplary embodiment of the present invention recognizes an FN fragment, it does not react with natural FN which exists for example in serum, that is, it does not react with full length FN, and is markedly useful in view of this point.

The antibody of an exemplary embodiment of the present invention can specifically measure an FN fragment without being affected by human FN contaminating in serum, even in a serum-containing sample, for example. Accordingly, it is possible to measure, specifically and with a high sensitivity, an FN fragment in an extract or culture supernatant of a human cultured cell which is cultured using a medium containing human FN derived from blood components such as human blood, serum, plasma or the like. For example, the concentration of an FN fragment can be monitored even when a medium containing human serum is used in the case of a gene transfection into a cell or cell culture using the FN fragment. Further, it is also useful in the high sensitivity measurement and monitoring of an FN fragment in a living body sample such as a blood sample. In addition, when a gene-transfected or cultured cell using an FN fragment is introduced into the living body, the FN fragment in the living body contaminated with the cell can be monitored.

In addition, the antibody of an exemplary embodiment of the present invention can be used for the monitoring of the production of an antibody for an FN fragment in the living body. For example, an anti-FN fragment antibody produced in the living body can be detected by using a plate to which the FN fragment was immobilized and allowing a living body-derived sample such as human serum or the like to compete with the antibody of an exemplary embodiment of the present invention. There is a case in which the living body produces an autoantibody for FN due to the abnormality of immune system and the like. In that case, a detection system which uses an antibody that specifically reacts with an FN fragment is effective for specifically finding out the production of an antibody for the FN fragment.

The FN fragment with which the antibody of an exemplary embodiment of the present invention reacts is a polypeptide containing the cell-binding domain of FN which is one of the seven domains of FN. That is, the FN fragment with which the antibody of an exemplary embodiment of the present invention reacts is a fragment containing at least a part of the cell adhesion domain constituted from the III-8, 9 and 10 of FN. The chain length of this FN fragment is, for example, from 50 to 1,500 amino acid residues, preferably from 100 to 1,000 amino acid residues, more preferably from 200 to 800 amino acid residues, particularly preferably from 250 to 600 amino acid residues. For example, the CH-296 and C-274 described in the aforementioned Non-patent Document 1 and the CHV-89, CHV-92 and CHV-181 described in Patent Document 2 are exemplified. The aforementioned CH-296 is on the market under the name of Retronectin®. Amino acid sequences of CH-296, C-274, CHV-89, CHV-92 and CHV-181 are described in SEQ ID NO:1, SEQ ID NO:2, SEQ ID NO:4, SEQ ID NO:5 and SEQ ID NO: 6 of SEQUENCE LISTING, respectively.

The antibody of the present invention reacts with at least one of the above FN fragments but does not react with FN.

Also, fragments such as F(ab')$_2$, Fab', Fab and the like obtained by allowing proteolytic enzymes such as pepsin, papain and the like to act upon the antibody of the present invention, thereby removing Fc region of the antibody, are also included in the antibody used in the present invention.

In addition, it may be a recombinant antibody produced by a genetic engineering means or a chimeric antibody in which its constant region is replaced with a constant region of other antibody, prepared based on the obtained monoclonal antibody. A bispecific antibody (bivalent antibody), scFv, Fab$_3$, Diabody, Triabody, Tetrabody, Minibody, Bis-scFv, (scFv)$_2$-Fc and intact-IgG are exemplified as such antibodies and are described in detail by Holliger et al., Nature Biotechnology, vol. 23, no. 9, pp. 1126-36 (2005), the entire contents thereof being hereby incorporated by reference.

The monoclonal antibody of an exemplary embodiment of the present invention can be produced making use of a hybridoma prepared by so-called cell fusion method. The aforementioned hybridoma is established for the first time by forming a fusion hybridoma of a group of antibody producing cells and a myeloma cell, cloning said hybridoma, selecting clones which produce antibodies that recognize an FN fragment and further selecting a clone suitable for the purpose of the present invention.

Spleen cell, lymph node cell, B lymphocyte and the like of an animal which is immunized with an FN fragment or a part thereof can be used as an antibody producing cell. As the animal to be immunized, mouse, rat, guinea pig, hamster, horse, goat, rabbit and the like can be exemplified. The aforementioned FN fragment to be used as the immunogen can be prepared as a recombinant protein by a genetic engineering mean using a gene coding for the FN fragment. It can also be prepared by artificially synthesizing a polypeptide of the FN fragment or a part thereof. The thus obtained FN fragment or a part thereof is directly used as such and independently for immunization of an animal. In addition, it may be used for the immunization of an animal by combining it with a carrier protein such as KLH (Key hole Limpet Hemocyanin) or mixing with PVP (polyvinyl pyrrolidone), and then mixing it with Freund's adjuvant. Alternatively, the FN fragment or a part thereof is directly mixed with Freund's adjuvant and used for the immunization of an animal. The immunization is carried out by subcutaneously, intramuscularly or intraperitoneally administering from 20 to 200 μg of an antigen-adjuvant mixture per once to the animal. For example, by administering the antigen-adjuvant mixture three to seven times at an interval of once in two to three weeks, the antibody producing cell can be fractionated from the spleen of immunized animal after about three to five days from the final immunization hi addition, by administering the antigen-adjuvant mixture once, the antibody producing cell can be fractionated from the lymph node of the immunized animal two or three weeks thereafter.

As the myeloma cell, those derived from mouse, rat, human and the like are used. The cell fusion is carried out by the method described by G. Kehler, Nature, vol. 256, page 495 (1975) or a method equivalent thereto, the entire contents thereof being hereby incorporated by reference. In that case, using 30 to 50% polyethylene glycol (molecular weight of 1,000 to 6,000), the antibody producing cell and myeloma cell are reacted at a temperature of from 30 to 40° C. for about one to three minutes. The hybridomas obtained by the cell fusion are subjected to screening. For example, hybridomas which produce antibodies capable of reacting with the FN fragment CH-296 that contains the amino acid sequence represented by the aforementioned SEQ ID NO:1 of SEQUENCE LISTING are screened by an enzyme immunoassay method (ETA) or the like using a human FN fragment as the antigen. Then hybridomas which produce antibodies that do not react with full length FN are screened. The thus obtained antibody producing hybridomas are cloned for example by the limiting dilution method. The thus obtained clones are then subjected to a screening by for example an enzyme immunoassay method or the like, in order to select a clone which produces the high sensitivity and high specificity monoclonal antibody of interest.

The thus selected clone is transplanted into the abdominal cavity of BALB/c mouse to which pristane (2,6,10,14-tetramethylpentadecane) or FIA (Freund incomplete adjuvant) is administered in advance, and peritoneal fluid containing the monoclonal antibody in high concentration is collected 10 to 14 days thereafter. The monoclonal antibody can be recovered from this peritoneal fluid by methods such as ammonium sulfate fractionation, polyethylene glycol fractionation, ion exchange chromatography, gel chromatography, affinity chromatography which are conventionally known as immunoglobulin purification methods.

For example, as an embodiment of the present invention, a monoclonal antibody RNIIC57Z 71-3A produced by a hybridoma cell RNIIC57Z 71-3A can be exemplified as the anti-FN fragment monoclonal antibody which reacts with human FN fragment but does not react with FN. The hybridoma cell RNIIC57Z 71-3A has been deposited as FERM P-21747 (original deposition date: Dec. 10, 2008) and as FERM BP-11202 (international deposition date: Dec. 9, 2009) in International Patent Organism Depositary, National Institute of Advanced Industrial Science and Technology (Chuo 6, 1-1-1 Higashi, Tsukuba, Ibaraki (postal code 305-8566)).

The aforementioned monoclonal antibody possesses a surprising function that it recognizes FN fragments having the amino acid sequence described in SEQ ID NO:2 of SEQUENCE LISTING but does not recognize the FN containing the same amino acid sequence (natural FN). A regent for measuring an FN fragment containing the antibody has a remarkable characteristic property that it reacts with each of the FN fragments CH-296, C-274, CHV-89, CHV-92 and CHV-181, which are the human FN fragments having the amino acid sequence described in SEQ ID NO:2 of SEQUENCE LISTING, but does not react with the FN having the aforementioned amino acid sequence. Thus, the regent can be applied broadly to fractionation of FN fragments from FN and measurement of FN fragments.

The present invention includes the aforementioned antibody producing cell, namely a hybridoma cell RNIIC57Z 71-3A which produces the monoclonal antibody RNIIC57Z 71-3A of the present invention.

(2) Regent for Measuring an FN Fragment of the Present Invention

The regent for measuring an FN fragment of the present invention is a reagent for measuring an FN fragment in a sample, which contains the FN fragment monoclonal antibody described in the aforementioned (1).

The measuring reagent of the present invention does not react with full length FN, even in the case of a sample contaminated with FN, such as a sample including blood components such as human blood, serum, plasma or the like or urine. Thus, it is possible to measure an FN fragment specifically with high sensitivity without being affected by the contaminated FN. Therefore, an FN fragment in an extract or culture supernatant of a human cultured cell which is cultured using a medium containing human FN such as of human blood, serum, plasma and the like can be measured specifically with high sensitivity. By an embodiment of the measuring method of the present invention, an FN fragment can be specifically measured even in the case of a sample containing FN in a high concentration of 1 μg/ml or more. Thus, for example, the concentration of an FN fragment can be monitored, even when a medium containing human serum is used for a gene transfection into a cell or a cell culture using the FN fragment.

In a preferable embodiment of the present invention, the measuring reagent of the present invention can measure human FN fragments having the amino acid sequence described in SEQ ID NO:2 of SEQUENCE LISTING (for example, CH-296, C-274, CHV-89, CHV-92, CHV-181 and the like) discriminating from FN.

An embodiment of the present invention relates to a regent for measuring an FN fragment which further contains an antibody which reacts with a human FN fragment. The antibody which reacts with a human FN fragment may be a polyclonal antibody or may be a monoclonal antibody, as long as it reacts with at least one of the fragments described above. Further, the antibody which reacts with a human FN fragment may be an appropriate antibody selected from anti-human FN polyclonal antibodies or known anti-human FN monoclonal antibodies. For example, the monoclonal antibody FN 30-8 produced by the hybridoma cell FN 30-8 is preferably used. The monoclonal antibody FN 30-8 is an example of a monoclonal antibody having a binding ability for C-274 and FN, which can be prepared from the hybridoma FN 30-8 by the method described in Experimental Cell Research, 1989, Vol. 185, pp 229-236. The monoclonal antibody FN 30-8 is sold by Takara Bio Inc. (product code: M010).

The measuring reagent of an exemplary embodiment of the present invention can detect an FN fragment which exists at a low concentration of about 3 ng/ml.

The sample to be measured by the measuring reagent of the present invention is not particularly limited, and body fluids such as blood plasma, serum, urine and the like, a cell, a cell extract, a cell culture supernatant and the like can be exemplified. The aforementioned sample is not particularly limited with the proviso that it is a sample which can be measured by the measuring reagent of the present invention, and a human-derived sample can be mentioned for example.

A preferable embodiment of the measuring reagent of the present invention is a regent for measuring an FN fragment which can be used in enzyme immunoassay including enzyme-linked immunosorbent assay (ELISA) as the measuring method. As an embodiment thereof, there can be exemplified a measuring reagent for detecting an FN fragment by a double antibody sandwich method which uses two kinds of antibodies that recognize the FN fragment. As an example of such a reagent, there can be mentioned a measuring reagent which uses the anti-FN fragment monoclonal antibody described in the aforementioned (1) and the monoclonal antibody FN 30-8 as its two composing components. Of these antibodies, one can be used as a solid phase antibody (primary antibody), and the other as a labeled antibody (secondary antibody). In this case, the solid phase antibody means an antibody immobilized on an appropriate insoluble carrier, and the labeled antibody means an antibody labeled with an appropriate label. The solid phase antibody is used for trapping an FN fragment as a substance to be tested in the sample, by its antigen-antibody reaction with the FN fragment. The labeled antibody is used for detecting the trapped aforementioned substance to be tested. Particularly, a measuring reagent, which uses the anti-FN fragment monoclonal antibody described in (1) as the solid phase antibody, and the monoclonal antibody FN 30-8 as the labeled antibody, can be used suitably. The measuring reagent of this embodiment can specifically trap a human FN fragment having the amino acid sequence described in SEQ NO:2 even when the sample contains the full length human FN, and can specifically measure the aforementioned human FN fragment without causing masking of the solid phase antibody by full length FN and without being affected by cross-species of the labeled antibody.

The measuring reagent of the present invention, which reacts with an FN fragment but does not react with FN, to be used in the aforementioned double antibody sandwich method, is a measuring reagent that uses two kinds of antibodies. Since specificities of these antibodies are very similar because each of them recognizes the small difference between an FN fragment and FN, it is almost impossible to construct a measuring reagent which can be used in the double antibody sandwich method. It is not always possible to find a combination of a solid phase antibody and a labeled antibody even when successive cross-reaction and addition recovery tests are carried out.

Though the monoclonal antibody to be used in the present invention is not particularly limited, a labeled antibody is prepared by labeling it using a radioisotope, an enzyme, a fluorescent material, an illuminant, a protein and the like. As the radioisotope, it is not particularly limited, but for example, [$^{125}$I], [$^{131}$I], [$^{3}$H], [$^{14}$C] and the like are preferable. Though the enzyme is not particularly limited, those which are stable and have a large specific activity are preferable, and for example, β-galactosidase, β-glucosidase, alkaline phosphatase, peroxidase, malate dehydrogenase and the like can be exemplified. Though the fluorescent material is not particularly limited, for example, fluorescamine, fluorescein isothiocyanate and the like can be exemplified. Though the illuminant is not particularly limited, for example, luminol, a luminol derivative, luciferin, lucigenin and the like can be exemplified. In addition, compounds such as biotin or the like can be used. In the measuring reagent of the present invention, the labeled antibody can be provided in various forms such as a solution, a freeze-dried product and the like.

The solid phase antibody is prepared by binding the measuring reagent of the present invention, which recognizes an FN fragment, to the surface of a carrier such as beads, microtiter plate, test tube, nitrocellulose membrane, nylon membrane or the like, using a method known to those skilled in the art. In addition, an antibody and a carrier for preparing the solid phase antibody and a reagent necessary for the immobilization may be provided before the stage of immobilization. An antibody to be used for the aforementioned object is also included in the solid phase antibody of the present invention.

The measuring reagent of the present invention may further contain a protecting agent, such as casein, BSA (bovine serum albumin) or the like. In addition, the measuring reagent of the present invention may further contain an antiseptic agent, such as sodium azide, Proclin or the like. An embodiment of the measuring reagent of the present invention may optionally contain various reagents, materials, tools and the like. It may also contain an adsorption plate for adsorbing the anti-FN fragment monoclonal antibody of the present invention or the antibody which reacts with a human FN fragment which constitute the measuring reagent of the present invention. In addition, it may also contain a reagent for detecting the labeled antibody (for example, a substrate such as TMBZ or the like) and a reagent to be used as a control (for example, a standard FN fragment as a standard for the concentration).

(3) Method for Measuring the FN Fragment of the Present Invention

The method for measuring an FN fragment of the present invention is a method in which the anti-FN fragment monoclonal antibody described in the aforementioned (1) or the reagent for measuring an FN fragment described in the aforementioned (2) is used. For example, an FN fragment can be measured by a competitive immunoassay using the monoclonal antibody of the present invention. Also, in the case of the double enzyme sandwich method using the measuring reagent of an embodiment of the present invention containing two kinds of monoclonal antibodies which uses one of the two monoclonal antibodies as the solid phase antibody and the other as the labeled antibody, an FN fragment can be measured by allowing a substance to be tested to contact with the solid phase antibody, further allowing to contact with the labeled antibody and detecting a complex of these monoclonal antibodies and the substance to be tested. Further, it may contain a step for washing the solid phase antibody after allowing it to contact with the substance to be tested and/or a step for removing the labeled antibody not combined with the substance to be tested by washing. Also, the solid phase antibody and labeled antibody are prepared by the operations of immobilization and labeling as described in the aforementioned (2). As an embodiment of the present invention, it is preferable to use the monoclonal antibody RNIIC57Z 71-3A and the monoclonal antibody FN 30-8. Further, a measuring system of the combination of the monoclonal antibody RNIIC57Z 71-3A as the solid phase antibody and the monoclonal antibody FN 30-8 as the labeled antibody is particularly preferable. A qualitative measurement and a quantitative measurement are included in the method of the present invention. As an embodiment, body fluids such as blood plasma, serum and the like, cell culture product and the like can be exemplified as the sample.

The method of an exemplary embodiment of the present invention can detect the FN fragment CH-296, which exists at a low concentration of about 3 ng/ml. The method of an exemplary embodiment of the present invention can perform a discrimination having markedly high specificity by using two kinds of monoclonal antibodies which recognize different regions of an FN fragment.

The following illustrative examples are used to further describe exemplary embodiments of the present invention, but the present invention is not limited to the following examples.

EXAMPLE 1

Preparation and Selection of Antibodies [1]

(1) Antigen Immunization and Cell Fusion

The FN fragment CH-296 (SEQ ID NO:1 of SEQUENCE LISTING) was prepared in accordance with the description of Non-patent Document 1 and used as an antigen solution of 1 mg/ml. The antigen solution was intraperitoneally administered to two of C57BL6 mice at a dose of 100 μg/shot/body after forming emulsion with complete Freund' adjuvant for the primary immunization, and on the second time and thereafter, a total of four boosters were carried out at intervals of two weeks by mixing with a commercially available water-soluble adjuvant (MI Adjuvant). Thereafter, final booster was carried out on all individuals after confirming the increase of antibody titer for each FN fragment in orbital vein serum. Three days after this final booster, the spleens of two mice were extracted, made into spleen cells by dispersing and washing with a serum-free medium and then mixed with a myeloma (P3U1) for cell fusion at a ratio of 5:1 (spleen cell:myeloma) and centrifuged, and the supernatant was removed to obtain cell pellet. A 1 ml of 50% PEG solution incubated at an appropriate temperature was added to this cell mixture at a constant rate and mixed while carrying out a slight shaking to a total of 3 ml. Thereafter, 7 ml of a serum-free medium was added thereto at a constant rate, and cell fusion was carried out by this operation.

From the above operation, various fused cells were obtained. An antibody specific to an antigen was screened from this wide variety of the population.

(2) HAT Selection

For the screening of the fused cells, a medium was prepared by adding HAT (H: hypoxanthine, A: aminopterin, T: thymidine) to a cloning medium (manufactured by Sanko Junyaku Co., Ltd.) and the medium was exchanged three times using this HAT medium starting from the next day of the fused day. The cells grown by this medium exchange operation were fused cells which possessed a spleen-derived de novo synthesis system and also immortalized.

(3) Screening

The immunogen, the FN fragment CH-296, was prepared at a concentration of 10 μg/ml phosphate buffered saline (PBS), added at 50 μl/well onto an immunoplate (manufactured by Nalge Nunc International) and allowed to stand overnight at 4° C. to effect its physical adsorption. FN purified from normal human plasma by gel filtration of gelatin column adsorption fractions was used as a blank antigen for evaluation in the screening and coated in the same manner at a concentration of 20 μg/ml PBS and at 50 μl/well. On the next day, the antigen solution was discarded, and a blocking operation was carried out by adding 25% blocker casein (manufactured by Pierce) at 200 μl/well and allowing to stand overnight at room temperature (20 to 30° C.). Thereafter, the blocking solution was discarded and the culture supernatants of fused cells obtained in the above-mentioned (2) (stock solution was used) were subjected to numbering and then charged into the immunoplate to carry out the primary reaction at room temperature (20 to 30° C.) for one hour. Each well after completion of the reaction was washed three times with PBS containing 0.1% Tween, and the liquid was sufficiently sucked up using paper towel. An anti-mouse IgG rat monoclonal antibody cocktail-peroxidase-labeled antibody was used for the detection. The aforementioned antibody was adjusted to 1 μg/ml and added thereto at 50 μl/well to carry out the reaction at room temperature (20 to 30° C.) for one hour. Thereafter, the labeled antibody liquid was discarded, and each well was washed four times with PBS. The washing liquid was sufficiently sucked up using paper towel, TMBZ (3,3',5,5'-tetramethylbenzidine) solution (manufactured by BioFX Laboratories Inc.) as a peroxidase substrate was added thereto at 50 μl/well, and the development of color was effected at room temperature for 15 to 30 minutes. The reaction was stopped by adding the same volume of 1 N sulfuric acid and then positive cell lines were verified with the naked eye and using a plate reader, subsequently attempting selection of cell lines which do not react with FN but specifically react with the FN fragment of interest.

(4) Selection and Cloning of Positive Cell Lines and Establishment of Cell Lines As a result of the strict screening as shown in (3), the cell lines which do not react with the FN antigen but specifically react with the FN fragments of interest were only eight colonies among 10,000 or more colonies contained in the tested 960 wells. Using these eight cell lines, cloning was immediately carried out by limiting dilution method. For each of the eight kinds of cloned anti-FN fragment antibody producing hybridoma, two clones (main cell line and sub-cell line) were respectively secured.

(5) Collection of Mouse Peritoneal Fluid

Master cells of both of the main cell line and sub-cell line of each of the aforementioned hybridoma clones having high specificity were kept as frozen cells and then, at almost the same time, each of the main cell lines was cultured in a large amount in the abdominal cavity of scid (T and B cells deletion type) mice to obtain crude antibody as peritoneal fluid. The peritoneal fluid was approximately from 3 to 5 ml per individual.

(6) Antibody Purification

The thus obtained peritoneal fluid was subjected to 50% saturated ammonium sulfate precipitation and dialysis, and the fraction was applied to a Protein A column. As the equilibration buffer, a high salt concentration buffer of 3 M NaCl, 1.5 M glycin-NaOH buffer (pH 8.9) was prepared, and a condition under which all subclasses of IgG can bind was employed. The fraction of the peritoneal fluid after the ammonium sulfate precipitation was diluted two times with the equilibration buffer and applied to the Protein A resin having almost the same volume of the peritoneal fluid, and the column was washed with the equilibration buffer until the absorbance at a wavelength of 280 nm became almost zero. Thereafter, elution was carried out by two steps of citrate buffer (pH 4.0) and citrate buffer (pH 3.0). The eluted fractions were immediately neutralized with 1 M Tris-HCl buffer (pH 9.0) and ammonium sulfate precipitation or centrifugation ultrafiltration concentration was carried out. The final antibody was dialyzed with PBS and sterilized by 0.22 μm filter filtration. Purity of the antibody was analyzed by 10% SDS-PAGE (reducing heating condition) to confirm that it was an antibody of excellent purity free from impurities other than the H chain and L chain.

(7) Purification of Antibodies by Different Techniques

In order to further broaden the choices in addition to the eight kinds of antibodies established in Example 1, three kinds of monoclonal antibodies which bind to the FN fragment C-274 or H-296 described in the Non-patent Document 1 were also prepared, in accordance with the method for preparing an anti-FN monoclonal antibody described in JP-B-6-44877 (Patent Document 1).

(8) Selection of Antibodies for the Construction of Measuring System

Peroxidase labeling was applied by a periodate method to a total of 11 kinds of antibodies including the eight kinds of antibodies obtained by the operations of the above-mentioned (1) to (6) and three kinds of antibodies obtained by the above-mentioned (7). The periodate method is a method in which sugar chain diol of peroxidase is subjected to dehydrogenation oxidation to form Schiff base and bind to the amino acid of the antibody. It was able to prepare enzyme-labeled antibodies for all of the antibodies under a state of keeping their binding activity with corresponding antigens. By combining these labeled antibodies with the solid phase antibodies of the same 11 kinds, total of 121 combinations were used for the screening of a system which can determine FN fragments. While some of the various combinations tested did not react with FN having a concentration of less than 1,000 ng/ml, all of them reacted with FN at a high concentration of 1,000 ng/ml or more, namely 1 μg/ml or more. It was extremely difficult in comparison with general cases to obtain an antibody which discriminates FN from an FN fragment, which have markedly similar antigen specificities. Since the difference in the structures of FN and an FN fragment is considerably small, a possibility was suggested that an FN fragment specific antibody capable of reacting with a similar epitope has been obtained.

EXAMPLE 2

Preparation and Selection of Antibodies [2]

(1) Preparation of New Antibodies

In addition to the FN fragment CH-296 of Example 1(1), the FN fragment C-274 (SEQ ID NO:2 of SEQUENCE LISTING) and the FN fragment H-296 were prepared in accordance with the description of Non-patent Document 1. An attempt was made to prepare antibodies which specifically react with these FN fragments, by the same methods of Example 1 (1) to (6). The FN fragments CH-296, C-274 and H-296, each having a concentration of 2 μg/ml PBS, were mixed and immobilized onto an immunoplate and used in the screening of antibodies. As a result of the screening, the cell lines which did not react with the FN antigens but specifically reacted with any one of the FN fragments CH-296, C-274 and H-296 were only six cell lines among 10,000 or more of the fused cell lines tested. In the same manner as in Example 1, two kinds of clones (main cell line and sub-cell line) were secured for the six cell lines and then subjected to peritoneal fluid formation using scid mice to prepare purified antibodies. Further, peroxidase-labeled antibodies were prepared by the same operation as Example 1(8).

(2) Selection of Antibodies for the Construction of a Measuring System

A system which can determine an FN fragment was screened using a total of 289 combinations in which the 11 kinds of antibodies used in the first screening and the six kinds of antibodies established by the second screening (a total of 17 kinds of antibodies) were respectively used as labeled antibodies and solid phase antibodies. By this screening, it was able at last to obtain one kind of the measuring system which can measure an FN fragment with high sensitivity without crossing with FN having a high concentration of 1 μg/ml. The combination was anti-RNIIC57Z 71-3A (FERM P-21747, FERM BP-11202) as the solid phase antibody and anti-FN 30-8 (manufactured by Takara Bio Inc.) as the labeled antibody.

(3) FN Fragment Measuring System

A measuring method which uses the established measuring system is shown below.

(A) A solution of the monoclonal antibody RNIIC57Z 71-3A prepared by diluting to 10 μg/ml with PBS is dispensed at 100 μl/well into an immunoplate equipment (manufactured by Nalge Nunc International) and allowed to stand overnight at 4° C.

(B) On the next day, the antibody solution is discarded and a 25% blocker casein/PBS solution (blocking solution) is dispensed at 200 μl/well and allowed to stand overnight at 4° C. to block a protein moiety to which the aforementioned antibody has not bound.

On the next day, the blocking solution is discarded and the plate is used in the following measurement.

(C) An analyte of a certain concentration is added to respective two rows of wells by 100 μl using a micropipette and allowed to undergo the reaction at room temperature (20 to 30° C.) for one hour. (First reaction)

(D) After discarding the reaction liquid and washing three times with 0.1% Tween 20-containing PBS, a 100 μl of enzyme-labeled antibody liquid of monoclonal antibody FN 30-8 is added to respective wells and allowed to undergo the reaction at room temperature (20 to 30° C.) for one hour. (Second reaction)

(E) After discarding the reaction liquid and washing four times with 0.1% Tween 20-containing PBS, a 100 μl of TMBZ solution is added to respective wells and allowed to undergo the reaction at room temperature (20 to 30° C.) for 20 minutes. (Coloring reaction)

(F) The reaction is stopped by adding 100 μl of 1 N sulfuric acid to respective wells in the same order of the addition of TMBZ solution, followed by thorough mixing.

After blank-correcting a microplate reader using distilled water as the control, the absorbance at a wavelength of 450 nm is measured.

After preparing a standard curve, concentration of the corresponding FN fragment is read from the absorbance of the analyte.

Table 1 shows a result of measurement carried out by the above-mentioned measuring system using the FN fragment CH-296 as the standard FN fragment. Necessary amount of the sample was 100 μl/well, and the FN fragment was detectable even at a concentration of 3.125 ng/ml.

TABLE 1

| Conc. (ng/ml) | 0 | 3.125 | 6.25 | 12.5 | 25 | 50 | 100 | 200 |
|---|---|---|---|---|---|---|---|---|
| Absorbance at 450 nm | 0.041 | 0.083 | 0.125 | 0.205 | 0.381 | 0.773 | 1.529 | 3.080 |
| Standard deviation (SD) | 0.002 | 0.001 | 0.003 | 0.003 | 0.004 | 0.001 | 0.010 | 0.021 |
| Coefficient of variation (CV [%]) | 5.2 | 1.7 | 2.3 | 1.4 | 1.1 | 0.2 | 0.6 | 0.7 |

(N = 2)

(4) Measurement of the Influence FN in Serum

The FN fragment CH-296 in various solvents was measured by the measuring system described in Example 2(2). As the solvents, 25% blocker casein/PBS solution, RPMI-1640 medium (manufactured by Sigma) containing 10% fetal bovine serum (manufactured by Lonza) and human serum were tested. Measured values of the absorbance at a wavelength of 450 nm are shown in Table 2. From the results of Table 2, it was shown that the above-mentioned measuring system is not inhibited by human serum or serum medium, and that it is possible to measure the FN fragment without reacting with FN contained in serum.

TABLE 2

| | Concentration of FN fragment CH-296 (ng/ml) | | | | | | | |
|---|---|---|---|---|---|---|---|---|
| Solvent | 0 | 15.625 | 31.25 | 62.5 | 125 | 250 | 500 | 1000 |
| 25% Blocker casein | 0.187 | 0.481 | 0.640 | 1.156 | 1.841 | 3.212 | 4.000 | 4.000 |
| Serum medium | 0.108 | 0.345 | 0.635 | 0.999 | 1.958 | 2.858 | 3.644 | 3.901 |
| Human serum | 0.059 | 0.342 | 0.612 | 1.059 | 1.768 | 2.960 | 3.916 | 4.000 |

(5) Measurement of Reaction with FN

Reaction with FN was measured by the measuring system described in Example 2(2). As the FN, FN in human serum, natural FN purified from human plasma and a commercially available FN (manufactured by Sigma) were tested. Reaction with serum FN is shown in Table 3, and reaction with natural FN and recombinant FN is shown in Table 4, as measured values of absorbance at a wavelength of 450 nm, As shown in the results in Table 3 and Table 4, it was shown that the above-mentioned measuring system does not react with serum FN and also does not react with FN of a extremely high concentration.

TABLE 3

| | Human serum dilution rate (times) | | | | | | |
|---|---|---|---|---|---|---|---|
| | 10 | 20 | 40 | 80 | 160 | 320 | 640 |
| Human serum | 0.124 | 0.072 | 0.056 | 0.058 | 0.067 | 0.058 | 0.075 |

TABLE 4

| | FN concentration (µg/ml) | | | | | | |
|---|---|---|---|---|---|---|---|
| | 0.46 | 0.93 | 1.87 | 3.76 | 7.5 | 15 | 30 |
| Natural type FN | 0.086 | 0.073 | 0.081 | 0.078 | 0.086 | 0.142 | 0.176 |
| Commercially available FN | 0.061 | 0.062 | 0.072 | 0.061 | 0.074 | 0.089 | 0.228 |

(6) Measurement of Reaction with FN Fragment

Reaction with various FN fragments was measured by the measuring system described in Example 2(2). As the FN fragments, CH-296 (SEQ ID NO:1 of SEQUENCE LISTING), C-274 (SEQ ID NO:2 of SEQUENCE LISTING), H-296 (SEQ ID NO:3 of SEQUENCE LISTING), CHV-89 (SEQ ID NO:4 of SEQUENCE LISTING), CHV-92 (SEQ ID NO:5 of SEQUENCE LISTING) and CI-IV-181 (SEQ ID NO:6 of SEQUENCE LISTING) were prepared. In addition, as their solvents, 25% blocker casein/PBS solution, a stock liquid [50% RPMI-1640 medium, 4% human serum albumin (manufactured by Sigma), 6% HES (hydroxyethyl starch), 5% DMSO (dimethyl sulfoxide)/physiological saline] and the stock liquid containing 0.1% Tween 20 were used. Each FN fragment was adjusted to 200 ng/ml using respective solvents. Measured values of absorbance at a wavelength of 450 nm are shown in Table 5. From the results of Table 5, it was shown that the above-mentioned measuring system can measure the FN fragments (274 to 574 amino acids) which contain cell adhesion domain of FN consisting of the amino acid sequence described in SEQ ID NO:2 of SEQUENCE LISTING and can measure the FN fragments in various solvents.

TABLE 5

| | Solvent | | |
|---|---|---|---|
| FN fragment | 25% Blocker casein | Stock liquid | Stock liquid containing 0.1% Tween 20 |
| CH-296 | 3.277 | 3.092 | 3.037 |
| C-274 | 3.597 | 2.373 | NT |
| H-296 | 0.004 | 0.026 | NT |
| CH-89 | 3.057 | 2.727 | NT |
| CHV-92 | 1.455 | 0.815 | NT |
| CHV-181 | 2.810 | 2.295 | NT |

NT: not tested

EXAMPLE 3

Measurement of FN Fragment in Washing Liquid of FN Fragment-Coated Dish

As the dish coated with the FN fragment CH-296, RetroNectin® Dish (manufactured by Takara Bio Inc.) was used. This dish was washed under the following two washing conditions A and B.

Washing condition A: A 1 ml of RPMI-1640 medium containing 10% fetal bovine serum is added to the dish and allowed to stand for 30 minutes. This operation is repeated three times.

Washing condition B: A 1 ml of PBS is added to the dish and allowed to stand for 30 minutes. This operation is repeated three times.

The washing liquid under each washing condition was recovered and the concentration of the FN fragment was measured by the measuring system described in Example 2(2). The concentration of the FN fragment is shown in Table 6. It was shown that the above-mentioned measuring system can be applied to the concentration measurement of the FN fragment contained in the washing liquid of FN fragment-coated dish.

TABLE 6

|  | Washing condition A | Washing condition B |
|---|---|---|
| First washing | 12.871 | 25.736 |
| Second washing | 3.613 | 5.098 |
| Third washing | 2.496 | 2.932 | n = 3

The results above show that the detection system which uses the anti-FN fragment antibody and the measuring reagent of the present invention is a system that can measure a human FN fragment specifically with high sensitivity and show stable performance.

The results obtained by measuring said FN fragment can provide useful information for the gene transfection method and cell culture method which use an FN fragment.

While the invention has been described in detail and with reference to specific embodiments thereof, it will be apparent to one skilled in the art that various changes and modifications can be made therein without departing from the scope thereof.

Sequence Listing Free Text

SEQ ID NO:1; Fibronectin fragment named CH-296.
SEQ ID NO:2; Fibronectin fragment named C-274.
SEQ ID NO:3; Fibronectin fragment named H-296.
SEQ ID NO:4; Fibronectin fragment named CHV-89.
SEQ ID NO:5; Fibronectin fragment named CHV-92
SEQ ID NO:6; Fibronectin fragment named CHV-181

---

What is claimed is:

1. A monoclonal antibody that specifically binds to a fragment of human fibronectin but does not specifically bind to human fibronectin, wherein the monoclonal antibody is monoclonal antibody RNIIC57Z 71-3A produced by the hybridoma cell RNIIC57Z 71-3A (FERM BP-11202).

2. A reagent for measuring a fragment of fibronectin in a sample, wherein the reagent comprises the monoclonal antibody of claim 1.

3. The reagent for measuring a fragment of fibronectin of claim 2, which further comprises an antibody which specifically binds to human fibronectin.

4. A method for measuring a fibronectin fragment in a sample, which comprises allowing the sample to contact with the anti-fibronectin fragment monoclonal antibody of claim 1; and detecting formation of a complex between the monoclonal antibody and any fibronectin fragment in the sample, thereby detecting the fibronectin fragment in the sample.

5. The method for measuring a fibronectin fragment of claim 4, wherein the fibronectin fragment is a human fibronectin fragment and the sample contains human fibronectin.

6. The method for measuring a fibronectin fragment of claim 4, wherein the sample is selected from the group consisting of a sample derived from a living body and a sample derived from a cultured cell.

7. The method for measuring a fibronectin fragment of claim 5, wherein the sample is selected from the group consisting of a sample derived from a living body and a sample derived from a cultured cell.

8. A method for measuring a fibronectin fragment in a sample, which comprises allowing the sample to contact with the reagent of claim 2; and detecting formation of a complex between the monoclonal antibody contained in the reagent and any fibronectin fragment in the sample, thereby detecting the fibronectin fragment in the sample.

9. The method for measuring a fibronectin fragment of claim 8, wherein the fibronectin fragment is a human fibronectin fragment and the sample contains human fibronectin.

10. The method for measuring a fibronectin fragment of claim 9, wherein the sample is selected from the group consisting of a sample derived from a living body and a sample derived from a cultured cell.

11. The method for measuring a fibronectin fragment of claim 8, wherein the sample is selected from the group consisting of a sample derived from a living body and a sample derived from a cultured cell.

12. A hybridoma cell having deposition number FERM BP-11202 which is capable of producing the monoclonal antibody of claim 1.

* * * * *